(12) United States Patent
Akiyama et al.

(10) Patent No.: US 10,006,849 B2
(45) Date of Patent: Jun. 26, 2018

(54) PARTICLE ANALYZER

(71) Applicant: SONY CORPORATION, Tokyo (JP)

(72) Inventors: Shoji Akiyama, Kanagawa (JP); Tatsumi Ito, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days. days.

(21) Appl. No.: 15/310,816

(22) PCT Filed: Apr. 10, 2015

(86) PCT No.: PCT/JP2015/061193
§ 371 (c)(1),
(2) Date: Nov. 14, 2016

(87) PCT Pub. No.: WO2015/178124
PCT Pub. Date: Nov. 26, 2015

(65) Prior Publication Data
US 2017/0074775 A1    Mar. 16, 2017

(30) Foreign Application Priority Data

May 22, 2014  (JP) ................. 2014-106366

(51) Int. Cl.
*G01N 15/14* (2006.01)
*G01N 35/10* (2006.01)

(52) U.S. Cl.
CPC ..... *G01N 15/1404* (2013.01); *G01N 35/1095* (2013.01); *G01N 2015/1409* (2013.01)

(58) Field of Classification Search
CPC ............... G01N 15/14; G01N 15/1404; G01N 2015/1409
See application file for complete search history.

(56) References Cited

U.S. PATENT DOCUMENTS

| 5,030,002 A * | 7/1991 | North, Jr. ........... G01N 15/1404 209/3.1 |
| 5,079,959 A * | 1/1992 | Miyake ............... G01N 15/1404 73/864.21 |
| 5,180,065 A * | 1/1993 | Touge ................ G01N 15/1404 209/3.1 |
| 5,275,787 A * | 1/1994 | Yuguchi ................ B01L 3/0268 209/579 |

(Continued)

FOREIGN PATENT DOCUMENTS

| JP | 01-067569 U | 1/1989 |
| JP | 01-067569 U | 5/1989 |

(Continued)

*Primary Examiner* — Sang Nguyen
(74) *Attorney, Agent, or Firm* — Chip Law Group

(57) ABSTRACT

Provided is a particle analyzer capable of suppressing mixture of other particles and analyzing particles with high accuracy. A sample liquid introducing member is disposed immediately below a flow cell of a particle analyzer in a manner movable in a forward direction and a reverse direction relative to a sample liquid introducing direction, and formed by integrating a suction nozzle adapted to suck sample liquid with a sample liquid introducing nozzle disposed inside an introducing unit of the flow cell and adapted to discharge the sucked sample liquid into the flow cell. Furthermore, a movement restriction mechanism adapted to restrict a moving amount of the sample liquid introducing member is provided.

10 Claims, 8 Drawing Sheets

(56) References Cited

U.S. PATENT DOCUMENTS

| | | | | |
|---|---|---|---|---|
| 6,263,745 B1* | 7/2001 | Buchanan | .......... | G01N 15/1404 |
| | | | | 73/865.5 |
| 6,657,713 B2* | 12/2003 | Hansen | .................. | G01N 15/14 |
| | | | | 209/639 |
| 7,867,778 B2* | 1/2011 | Hayenga | ................ | G01N 21/11 |
| | | | | 382/133 |
| 9,027,850 B2* | 5/2015 | Buchanan | .......... | G01N 15/1404 |
| | | | | 239/102.1 |
| 2011/0259749 A1* | 10/2011 | Kanda | .................... | G01N 15/14 |
| | | | | 204/600 |
| 2013/0258075 A1* | 10/2013 | Muraki | ................ | G01N 15/14 |
| | | | | 348/61 |
| 2014/0162347 A1* | 6/2014 | Alspektor | ................ | B05D 7/14 |
| | | | | 435/270 |
| 2014/0306122 A1* | 10/2014 | Norton | .................. | G01N 15/14 |
| | | | | 250/428 |

FOREIGN PATENT DOCUMENTS

| | | | |
|---|---|---|---|
| JP | 06-194299 A | 4/1994 | |
| JP | 06-194299 A | 7/1994 | |
| JP | 08-313426 A | 11/1996 | |
| JP | 09-318522 A | 12/1997 | |
| JP | 2010-230629 A | 10/2010 | |
| JP | 2012-118046 A | 6/2012 | |

* cited by examiner

PARTICLE ANALYZER

CROSS REFERENCE TO RELATED APPLICATIONS

This application is a U.S. National Phase of International Patent Application No. PCT/JP2015/061193 filed on Apr. 10, 2015, which claims priority benefit of Japanese Patent Application No. JP 2014-106366 filed in the Japan Patent Office on May 22, 2014. Each of the above-referenced applications is hereby incorporated herein by reference in its entirety.

TECHNICAL FIELD

The present technology relates to a particle analyzer. More specifically, the present technology relates to a technology adapted to individually analyze particles of a cell and the like by an optical technique and the like.

BACKGROUND ART

In related arts, an optical measurement method using flow cytometry (flow cytometer) is utilized to analyze biologically-relevant fine particles such as cells, microbes, liposomes, and the like. The flow cytometer is a device to irradiate fine particles flowing inside a flow passage formed in a flow cell, a microchip, and the like with light, and detect and analyze fluorescence and scattered light emitted from individual fine particles.

The flow cytometer in a related art is adapted to suck sample liquid stored in, for example, a container or a tube by using a sample injection mechanism, a pipetter, or the like and inject the sample liquid into a flow passage of the flow cell or the microchip (refer to Patent Documents 1 and 2). Furthermore, recently the particle analyzer such as the flow cytometer is totally automated, and for example, a device that can automatically perform sampling from a plurality of tubes or wells storing different samples respectively is developed.

CITATION LIST

Patent Documents

Patent Document 1: Japanese Patent Application Laid-Open No. 8-313426 A
Patent Document 2: Japanese Patent Application Laid-Open No. 2012-118046 A

SUMMARY OF THE INVENTION

Problems to be Solved by the Invention

However, a flow cytometer in above-described related arts has a configuration in which a sample nozzle of a flow cell is in communication with a sample injection mechanism via a liquid feeding tube, piping, and the like. Therefore, there may be a problem in which particles tend to stagnate at a joint portion thereof. Especially, the device that automatically performs sampling from a plurality of sample containers or wells has a configuration in which the sample injection mechanism and the like are moved so as not to influence an optical system. Therefore, a length of the liquid feeding tube and the like are further elongated, and clogging and stagnation of particles tend to occur.

In the event of clogging and stagnation of particles in the liquid feeding tube or piping, the particles may be mixed with another sample liquid subsequently sucked, and detection accuracy may be degraded. Additionally, in the flow cytometer, cleaning for a feeding system is generally performed in each sampling in order to prevent mixture of other particles, but when the liquid feeding tube or the like is formed long, an amount of cleaning liquid is increased and a time required for cleaning becomes longer.

Considering above, the present disclosure is directed to providing a particle analyzer capable of suppressing mixture of other particles and analyzing particles with high accuracy.

Solutions to Problems

A particle analyzer according to the present disclosure includes: a flow cell including: an introducing unit adapted to introduce sample liquid containing current analysis particles, and sheath liquid; and a detection unit in which a laminar flow formed of the sample liquid and the sheath liquid flows; a sample liquid introducing member disposed immediately below the flow cell in a manner movable in a forward direction and a reverse direction relative to a sample liquid introducing direction, and formed by integrating suction nozzle adapted to suck sample liquid with a sample liquid introducing nozzle disposed inside the introducing unit of the flow cell and adapted to discharge the sucked sample liquid into the flow cell; and a movement restriction mechanism adapted to restrict a moving amount of the sample liquid introducing member.

The movement restriction mechanism is, for example, a rib portion provided on an outer surface of the sample liquid introducing nozzle.

Furthermore, the movement restriction mechanism may also have a configuration including: a position sensor adapted to detect positional change of the sample liquid introducing member; and a sample stage control unit adapted to control, on the basis of a detection result of the position sensor, movement of a sample stage on which a container storing the sample liquid is placed.

In this case, for example, the sample stage control unit stops upward movement of the sample stage in the case where the position sensor detects upward movement of the sample liquid introducing member.

Furthermore, the sample liquid introducing nozzle may also be fixed to the introducing unit of the flow cell via a spring material or an elastic material.

In the particle analyzer of the present disclosure, a block member may be attached to an outer surface of the suction nozzle.

In this case, a position of the block member may be moved upward and downward in accordance with upward movement and downward movement of the sample stage on which the container storing the sample liquid is placed.

Furthermore, a flow passage where cleaning liquid flows is formed inside the block member, and cleaning for the outer surface of the suction nozzle can be performed by moving upward and downward along the outer surface of the suction nozzle.

Effects of the Invention

According to the present disclosure, particles can be analyzed with high accuracy because mixture of other particles can be suppressed. Note that effects recited herein are not necessarily limited thereto and may also be any of those recited in the present disclosure.

MODE FOR CARRYING OUT THE INVENTION

In the following, embodiments to implement the present disclosure will be described in detail with reference to the attached drawings. Note that the present disclosure is not limited to the respective embodiments described below. Additionally, note that the description will be provided in the following order.

Figure 1:
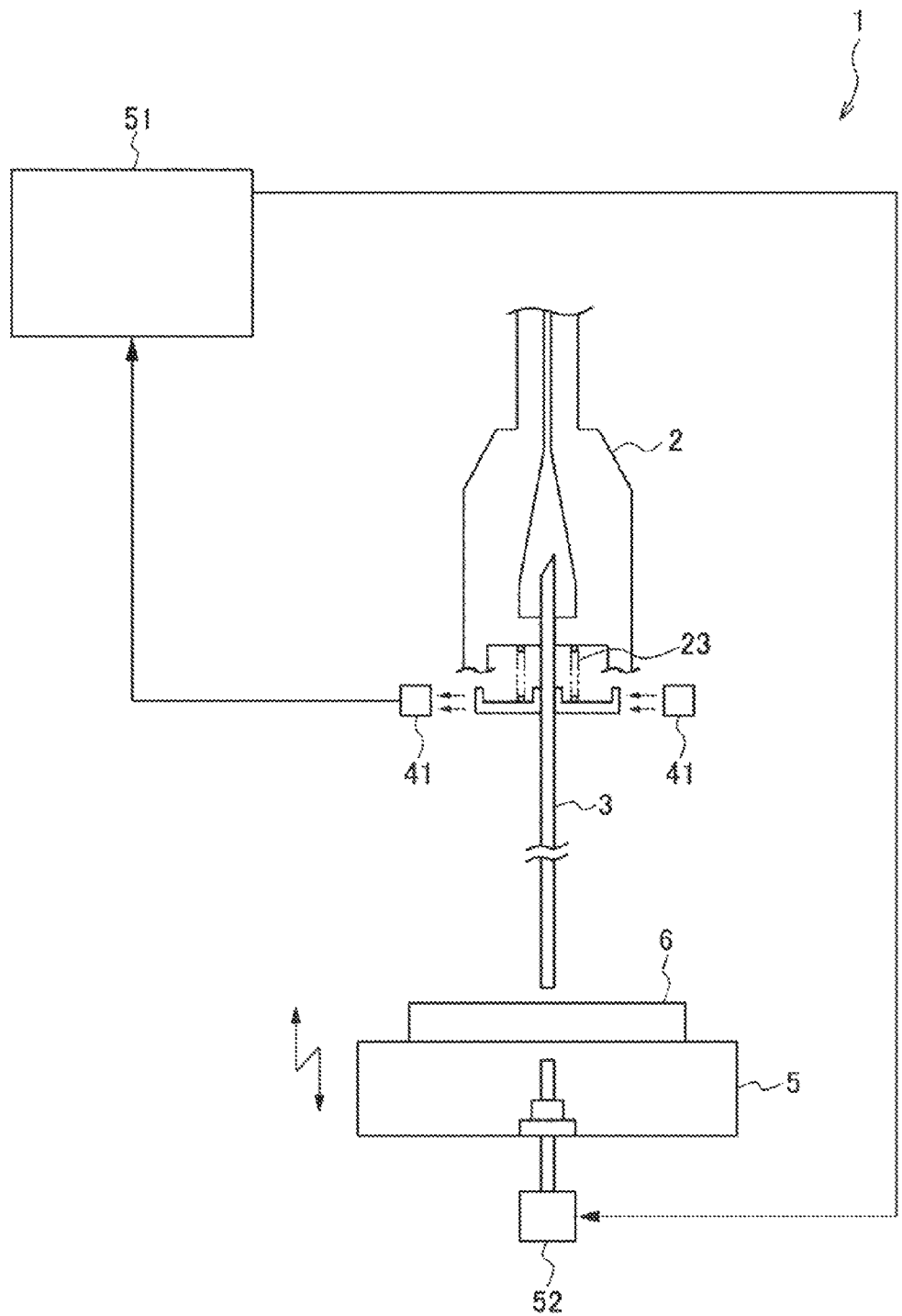
FIG. 1 is a schematic diagram illustrating an entire configuration of a particle analyzer according to a first embodiment of the present disclosure.
Figure 2:
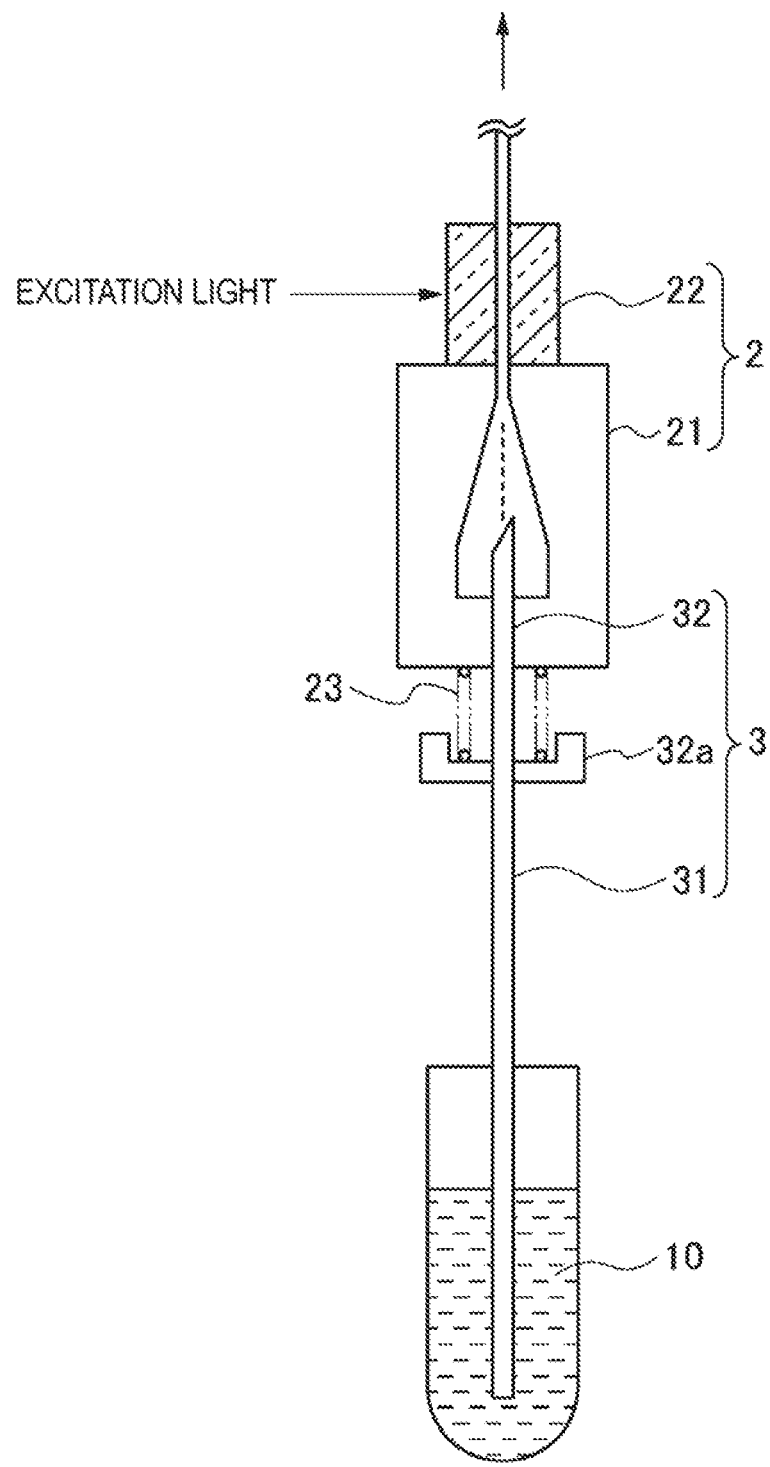
FIG. 2 is an enlarged view of a flow system of a particle analyzer 1 illustrated in FIG. 1.
Figure 3:
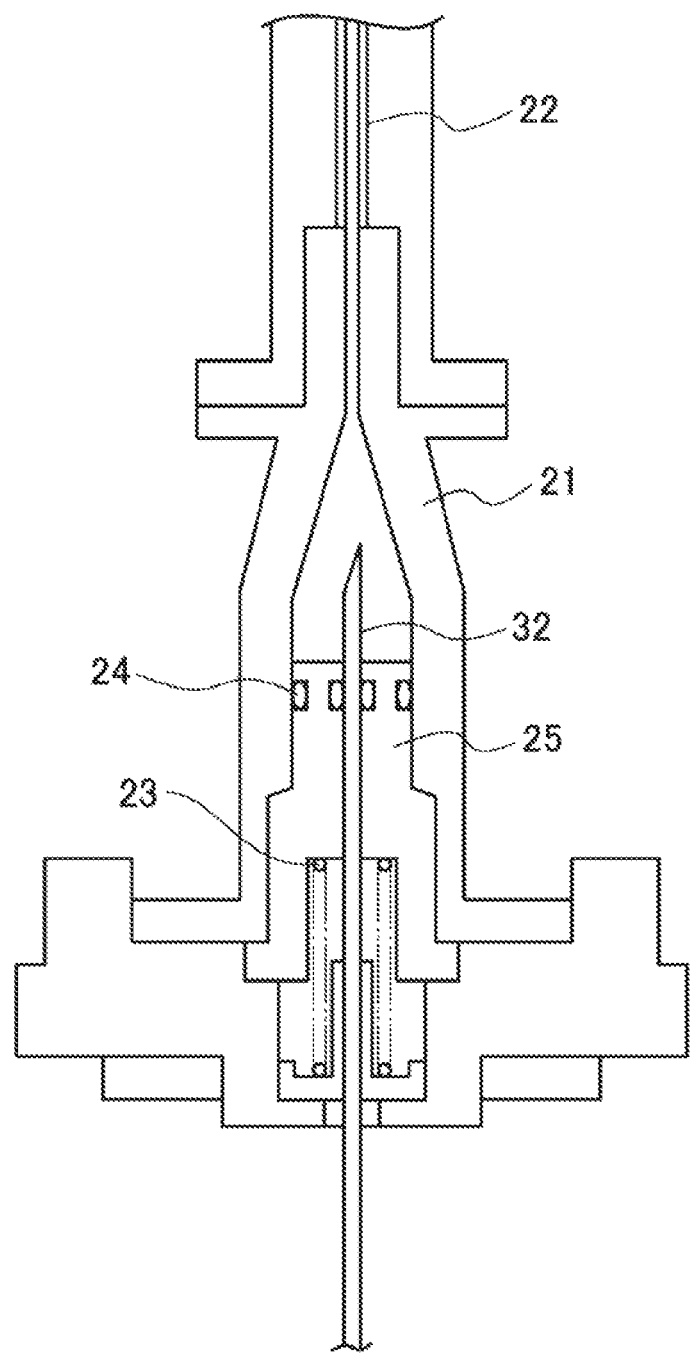
FIG. 3 is an enlarged cross-sectional view illustrating inside of a flow cell illustrated in FIG. 1.

1. First Embodiment
(Exemplary Particle Analyzer Including Sample Liquid Introducing Member Integrally Formed)
2. Second Embodiment
(Exemplary Particle Analyzer Having Suction Nozzle Attached With Block Member)
1. First Embodiment First, a particle analyzer according to a first embodiment of the present disclosure will be described. FIG. 1 is a schematic diagram illustrating an entire configuration of the particle analyzer according to the present embodiment. FIG. 2 is an enlarged view of a flow system of a particle analyzer 1, and FIG. 3 is an enlarged cross-sectional view illustrating the inside of a flow cell 2.

[Entire Configuration of Device]

The particle analyzer 1 of the present embodiment is adapted to analyze particles flowing in a flow passage by an optical technique and the like, and includes the flow cell 2, a sample liquid introducing member 3, a movement restriction mechanism 4, a sample stage 5, and the like as illustrated in FIG. 1.

[Regarding Particles]

Particles to be analyzed by the particle analyzer 1 of the present embodiment include biologically-relevant fine particles such as cells, microbes, and ribosomes, or synthetic particles such as latex particles, gel particles, and particles for industrial use, and the like.

The biologically-relevant fine particles include chromosomes, ribosomes, mitochondrion, organelle (cell organelle), and the like constituting various kinds of cells. Furthermore, the cells include plant cells, animal cells, hematopoietic cells, and the like. Additionally, the microbes include bacteria such as coli bacilli, viruses such as tobacco mosaic viruses, and fungi such as yeast. The biologically-relevant fine particles may include biologically-relevant polymers such as nucleic acids, proteins, and complexes thereof.

On the other hand, as the particles for industrial use, particles formed of organic polymeric materials, inorganic materials, metallic materials, or the like may be exemplified. As the organic polymeric materials, polystyrene, styrene-divinylbenzene, polymethyl methacrylate, and the like may be used. Also, as the inorganic materials, glass, silica, magnetic materials, and the like may be used. As the metallic material, for example, gold colloid, aluminum, and the like may be used. Note that these fine particles generally have spherical shapes, but may also have a non-spherical shape, and furthermore, a size, mass, and the like thereof are not particularly limited.

[Flow Cell 2]

As illustrated in FIGS. 2 and 3, the flow cell 2 is formed of sample liquid 10 containing current analysis particles, an introducing unit 21 into which sheath liquid around the sample liquid is introduced, and a detection unit 22 in which a laminar flow formed of the sample liquid and the sheath liquid flows. Furthermore, the detection unit 22 is irradiated with excitation light such as laser light, and particles are analyzed by detecting scattered light and fluorescence emitted from particles irradiated with the excitation light.

Preferably, the detection unit 22 of the flow cell 2 includes a material having transmissivity for the excitation light and is formed of a material having little self-fluorescence, small wavelength dispersion, and a little optical difference, and generally formed of glass, quartz, and the like. As illustrated in FIG. 3, packing 24 such as an O-ring may also be attached to the inside of the flow cell 2 for preventing liquid leakage, and additionally, a guide 25 or a spring material 23 to fix the sample liquid introducing member 3 may also be provided.

[Sample Liquid Introducing Member 3]

The sample liquid introducing member 3 is formed of a suction nozzle 31 adapted to suck the sample liquid 10, a sample liquid introducing nozzle 32 adapted to discharge the sucked sample liquid 10 into the flow cell 2, and the suction nozzle 31 and the sample liquid introducing nozzle 32 are integrally formed in a linear shape. By integrally forming the suction nozzle 31 and the sample liquid introducing nozzle 32, there is no joint portion formed. Moreover, by forming these components in a linear shape, a distance from a tip of the suction nozzle 31 to the flow cell 2 is shortened and there is no curved portion formed. Therefore, stagnation of particles hardly occurs.

The sample liquid introducing member 3 is disposed immediately below the flow cell 2, and the sample liquid introducing nozzle 32 is inserted into the introducing unit 21 and fixed with the spring material 23. Thus, since the sample liquid introducing member 3 is fixed with the spring material 23, the sample liquid introducing member 3 can be moved in a forward direction and a reverse direction relative to a sample liquid introducing direction. Meanwhile, fixation of the sample liquid introducing member 3 is not limited to the spring material 23, and an elastic material such as rubber may also be used.

[Movement Restriction Mechanism]

The movement restriction mechanism is adapted to restrict a moving amount of the sample liquid introducing member 3, and is formed of, for example, a rib portion 32a provided on an outer surface of the sample liquid introducing nozzle 32, a position detection sensor 41, a sample stage control unit 51, and the like. For example, the rib portion 32a is provided in a circumferential direction of the sample liquid introducing nozzle 32, and the rib portion 32a contacts a projecting porting portion provided inside the flow cell 2, thereby restricting upward movement of the sample liquid introducing member 3.

Furthermore, for example, a pair of position detection sensors 41 is provided at positions facing each other, a position of the rib portion 32a of the sample liquid introducing nozzle 32 is detected by the position detection sensors 41, and whether the sample liquid introducing member 3 is moved is confirmed. Then, movement of the sample stage 5 on which a container 6 storing the sample liquid 10 is placed is controlled on the basis of a detection result of the position detection sensor 41.

Specifically, the pair of position detection sensors 41 detects whether the sample liquid introducing member 3 is moved upward. Then, in the case of detecting upward movement, it is determined that the tip of the suction nozzle 31 of the sample liquid introducing member 3 is contacting the container 6, and upward movement of the sample stage 5 is stopped by the sample stage control unit 51.

In the particle analyzer 1 of the present embodiment, sampling is performed by vertically and horizontally moving the sample stage 5. Therefore, the positions of the flow cell 2 and the sample liquid introducing member 3 are basically fixed. Therefore, in the case where upward movement of the sample liquid introducing nozzle 32 is detected by the position detection sensor 41, it can be considered that the tip of the suction nozzle 31 is contacting the container 6 because the sample stage 5 is moved too upward or a lid of the container 6 is kept attached.

In this case, the tip of the sample liquid introducing nozzle 32 is moved upward and contacts the introducing unit 21 or the detection unit 22 of the flow cell 2, and an optical system and detection accuracy may be influenced. Additionally, when the suction nozzle 31 contacts the container 6, the container 6 may be damaged or current analysis particles may be damaged.

Therefore, in the particle analyzer 1 of the present embodiment, further upward movement is controlled by the above-described rib portion 32a such that the sample liquid introducing member 3 is moved up to a predetermined position or higher, or by controlling the sample stage 5 with the sample stage control unit 51. By providing such a movement restriction mechanism, influence given by the suction nozzle 31 contacting the container 6 can be minimized.

[Sample Stage 5]

The sample stage 5 is a place where the container 6 storing the sample liquid 10 is placed, and can be moved by a motor 52 and the like in directions of X-axis, Y-axis, and Z-direction, namely, in the vertical and horizontal directions. Furthermore, the sample liquid is individually sampled from a plurality of wells or sample tubes by vertically and horizontally moving the sample stage 5, and analysis is performed.

[Operation]

Next, operation of the above-described particle analyzer 1 will be described. In the case of analyzing particles by using the particle analyzer 1 of the present embodiment, first the container 6 storing the sample liquid 10 is placed on the sample stage 5. As the container 6 used here, for example, a well plate in which a plurality of wells is formed on a substrate, a component in which a plurality of sample tubes is held by a holder, and the like may be exemplified, but not limited thereto.

Next, after positioning of the sample stage 5 is performed in the X-axis direction and the Y-axis direction, and the sample stage 5 is moved upward until the sample liquid 10 contacts the tip of the suction nozzle 31, and then the sample liquid 10 is sampled for first analysis. After the sample liquid 10 is sampled, the sample stage 5 is moved down. Then, the sampled sample liquid 10 is introduced into the flow cell 2 from the sample liquid introducing nozzle 32 and mixed with sheath liquid to form a laminar flow. After that, particles are irradiated with excitation light in the detection unit 22 and analyzed.

At this point, the position of the sample liquid introducing member 3 is monitored by the position detection sensor 41, and in the case where upward movement of the sample liquid introducing member 3 is detected, the motor 52 of the sample stage 5 is controlled by the sample stage control unit 51 and upward movement of the sample stage 5 is stopped. Furthermore, the sample liquid introducing member 3 is restricted so as not to be moved upward to the predetermined position or higher by the rib portion 32a provided at the sample liquid introducing member 3.

Additionally, in the case where upward movement of the sample liquid introducing member 3 is detected, the sample stage control unit 51 stops upward movement of the sample stage 5, and then may further move the sample stage 5 downward. At this point, the sample liquid introducing member 3 is returned to an original position by restoring force of the compressed spring material 23. Furthermore, in the case where upward movement of the sample liquid introducing member 3 is detected or when the sample stage 5 is moved down and returned to an original state, the particle analyzer 1 of the present embodiment may issue an alarm sound to provide a notification to a worker such as an operator.

As described in detail above, the suction nozzle and the sample liquid introducing nozzle are integrally formed in the particle analyzer of the present embodiment, and there is neither a joint portion nor a curved portion. Therefore, stagnation of particles hardly occurs. Furthermore, since the sample liquid introducing member is linearly formed and disposed immediately below the flow cell, a liquid feeding distance is shortened, cleaning can be performed in a short time, and also an amount of cleaning liquid to be used can be reduced.

In the case where the sample liquid introducing member and the container are disposed immediately below the flow cell, the sample liquid introducing member may contact the container at the time of sampling, and these components may be damaged. In contrast, in the particle analyzer of the present embodiment, since the sample liquid introducing member is movable in the vertical direction, influence given by contacting the container can be reduced, and damage can be prevented. In this case, there maybe concern that the flow cell and the optical system are influenced by upward movement of the sample liquid introducing member, but an upward moving amount of the sample liquid introducing member is restricted by the movement restriction mechanism in the particle analyzer of the present embodiment. Therefore, influence to the flow cell and the optical system can also be suppressed.

As a result, according to the particle analyzer of the present embodiment, mixture of other particles is suppressed, and particles can be analyzed with high accuracy.

2. Second Embodiment

Figure 4:
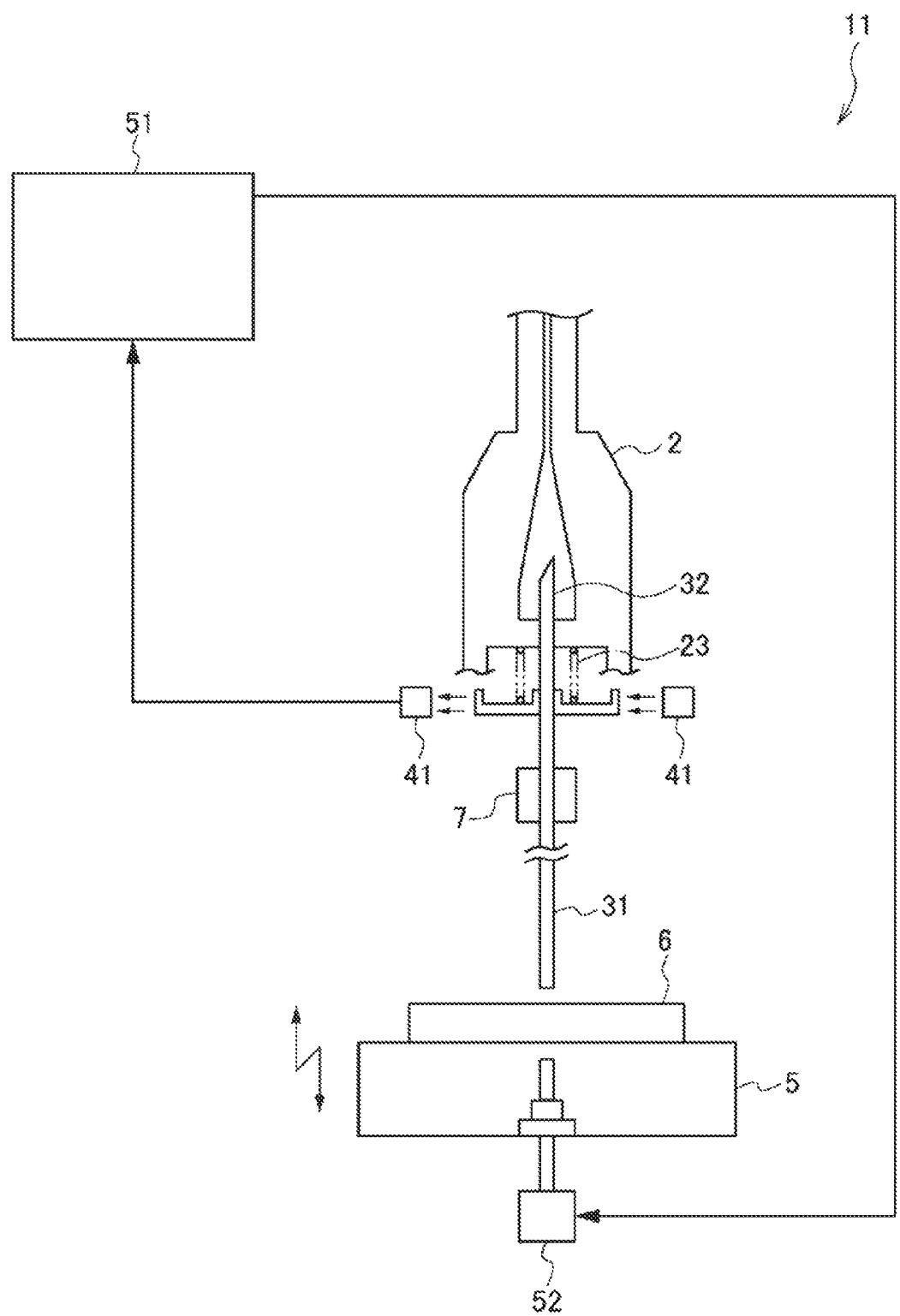
FIG. 4 is a schematic diagram illustrating an entire configuration of a particle analyzer according to a second embodiment of the present disclosure.
Figure 5:
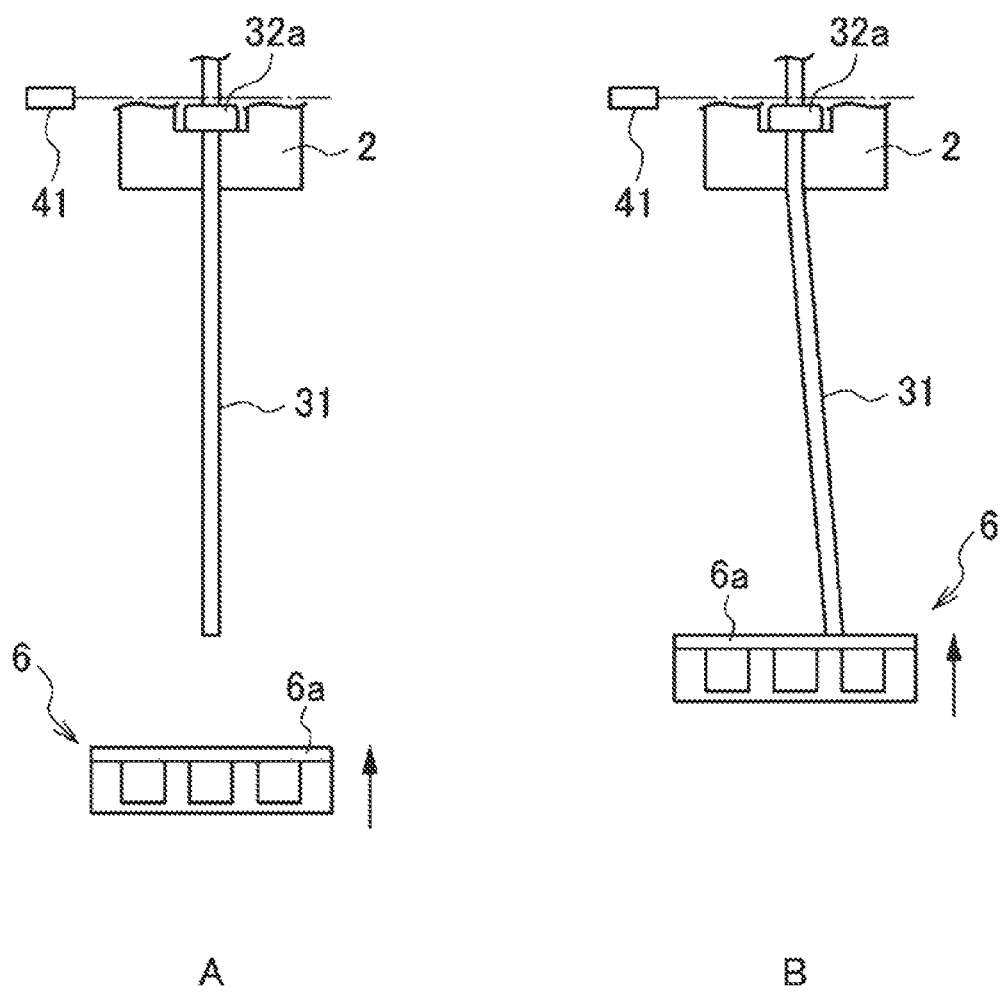
FIGS. 5A and 5B are diagrams illustrating exemplary operation in the case where a suction nozzle is long.
Figure 6:
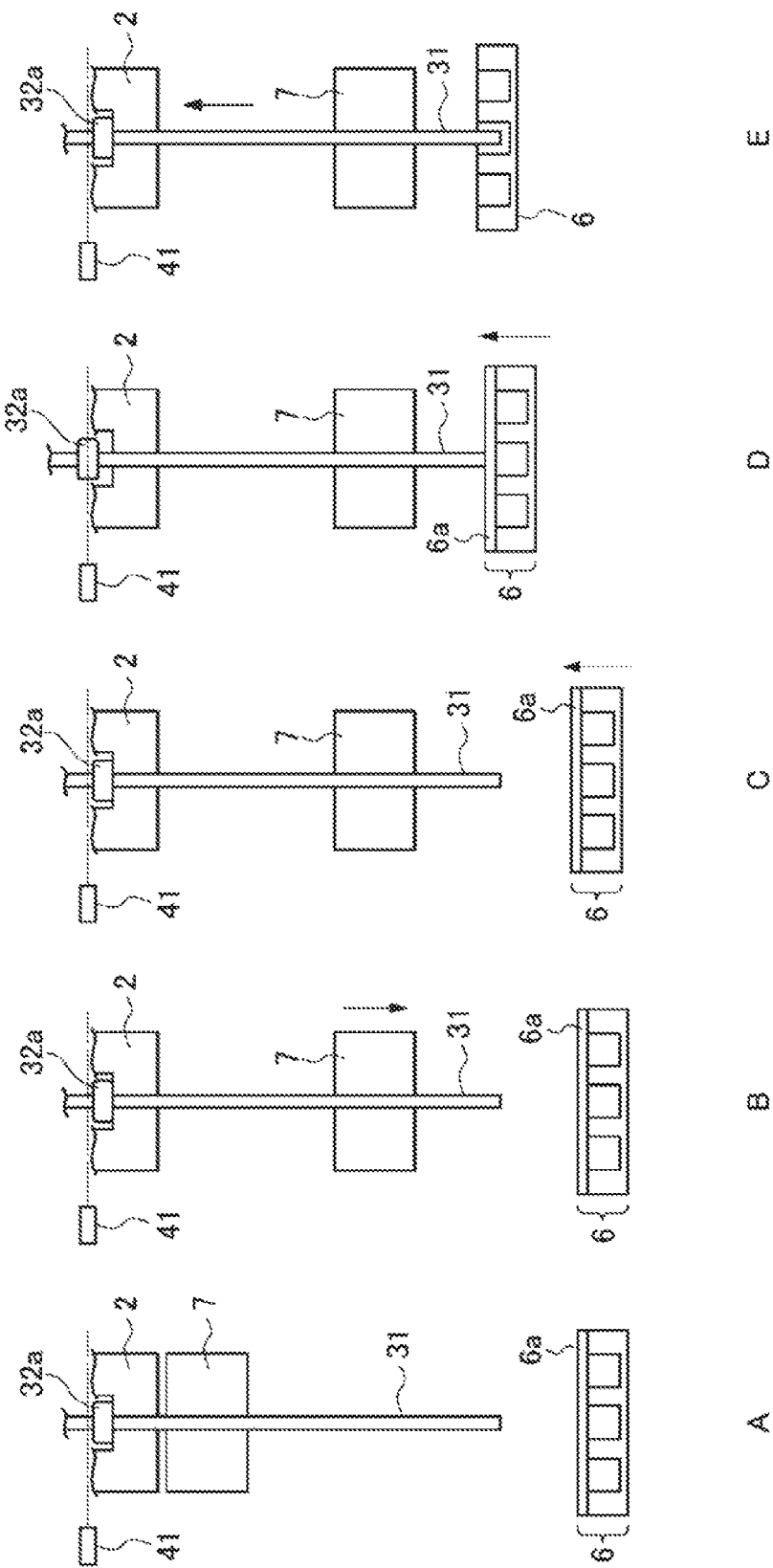
FIGS. 6A to 6E are schematic diagrams illustrating exemplary operation of a particle analyzer 11 illustrated in FIG. 4.
Figure 7:
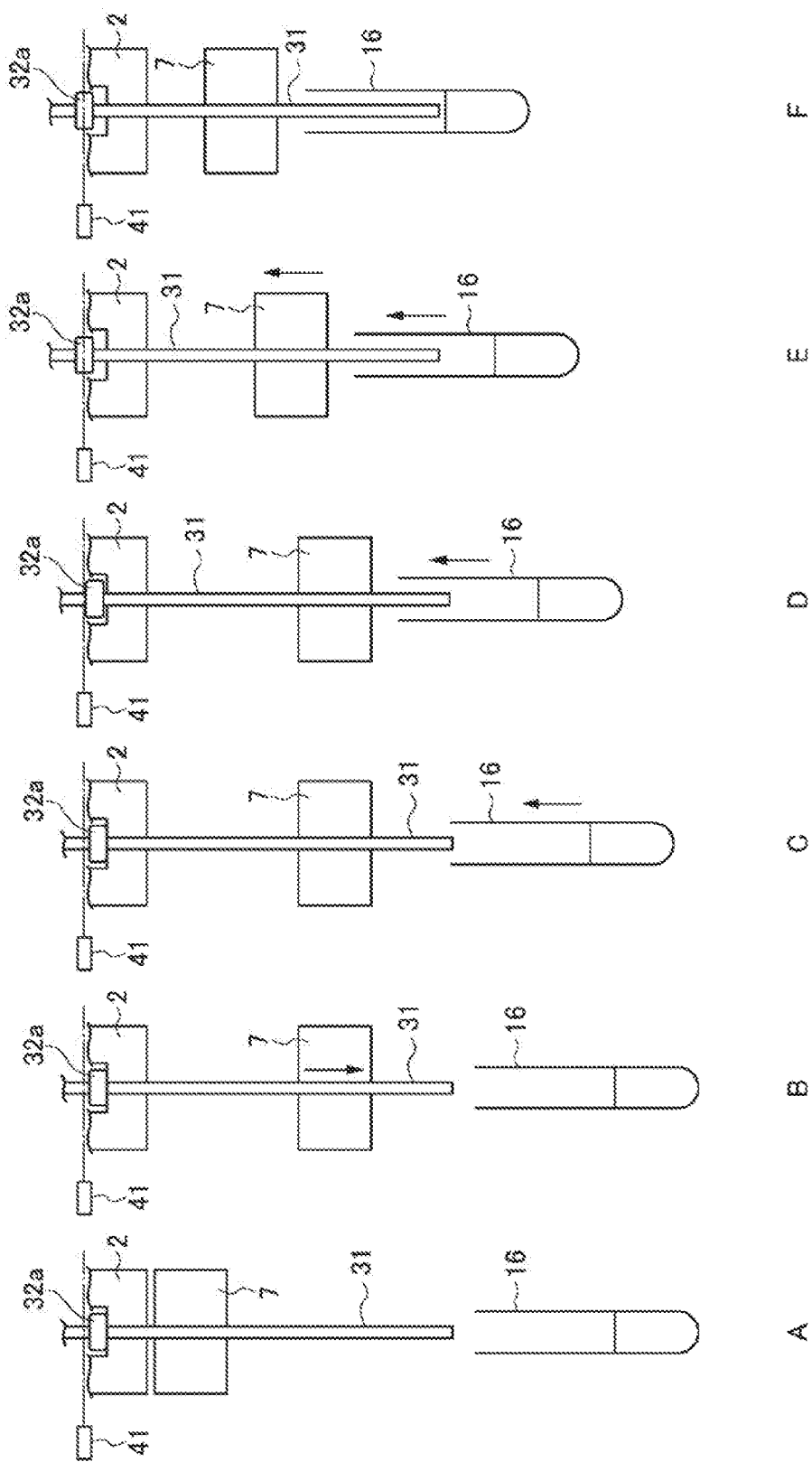
FIGS. 7A to 7F are schematic diagrams illustrating another exemplary operation of the particle analyzer 11 illustrated in FIG. 4.
Figure 8:
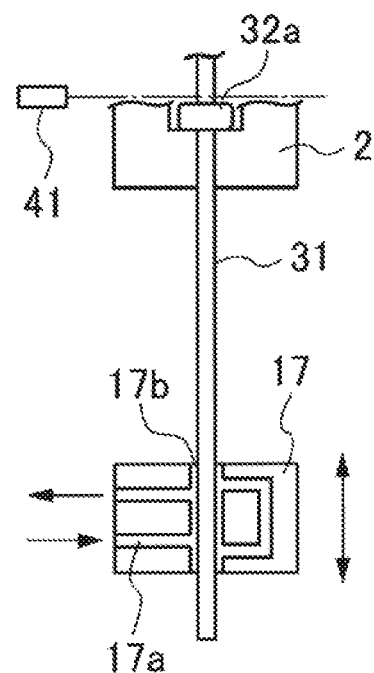
FIG. 8 is a schematic diagram illustrating a configuration of a block member having a cleaning function.

Next, a particle analyzer according to a second embodiment of the present disclosure will be described. FIG. 4 is a schematic diagram illustrating an entire configuration of the particle analyzer according to the present embodiment. Furthermore, FIGS. 5A and 5B are diagrams illustrating exemplary operation in the case where a suction nozzle is long, and FIGS. 6A to 6E and FIGS. 7A to 7F are schematic diagrams illustrating exemplary operation of a particle analyzer 11 illustrated in FIG. 4. Additionally, FIG. 8 is a schematic diagram illustrating another configuration of a block member. Meanwhile, in FIGS. 4 to 8, components same as those in a particle analyzer of a first embodiment illustrated in FIGS. 1 to 3 are denoted by the same reference signs, and a detailed description therefor will be omitted.

[Entire Configuration of Device]

As illustrated in FIG. 4, in the particle analyzer 11 of the present embodiment, the block member 7 is attached to an outer surface of a suction nozzle 31, and other portions are similar to the particle analyzer 1 of the first embodiment.

[Block Member 7]

For example, as illustrated in FIGS. 5A and 5B, in the case where a lid 6a is kept attached on a container 6, when the suction nozzle 31 has a long length, the suction nozzle 31 is curved and not moved upward even though a sample stage is moved upward and a tip of the suction nozzle 31 contacts the lid 6a. In this case, a position detection sensor 41 cannot detect contact between the suction nozzle 31 and the container 6 (lid 6a).

Therefore, in the particle analyzer 11 of the present embodiment, the block member 7 is attached to the outer surface of the suction nozzle 31 and prevents the suction nozzle from being curved or tilted. Here, the block member 7 may be formed of, for example, a metallic material such as stainless, or a resin material having an excellent chemical resistance property, such as a polyetheretherketone (PEEK) resin. Furthermore, a material having a chemical resistance property improved by surface treatment may also be used. Furthermore, a size and a shape of the block member 7 are not particularly limited and can be suitably set in accordance with a length and a thickness of the suction nozzle 31 and arrangement of other components.

As illustrated in FIGS. 6A to 6E, preferably, a position of the block member 7 is changed in response to upward movement and downward movement of the container 6. Specifically, as illustrated in FIGS. 6A and 6B, first the block member 7 located near a flow cell 2 is moved down to a predetermined position. After that, as illustrated in FIG. 6C, the container 6 is moved upward by operating the sample stage. At this point, the block member 7 is stopped and kept at the same position. Then, as illustrated in FIG. 6D, when the lid 6a of the container 6 contacts the tip of the suction nozzle 31, the position of the block member 7 is not changed and only the sample liquid introducing member (suction nozzle 31) is moved upward, and such movement is detected by the position detection sensor 41.

Meanwhile, as illustrated in FIG. 6E, the block member 7 may be stopped at the predetermined position during normal operation, but may also be moved upward and retracted to the vicinity of the flow cell 2 that is an initial position.

Furthermore, as illustrated in FIGS. 7A to 7F, the block member 7 can be moved upward and downward by setting estimated timing of impact (contact) in accordance with a container 16 designated by a user. Specifically, as illustrated in FIGS. 7A and 7B, first the block member 7 located near the flow cell 2 is moved down to the predetermined position. After that, as illustrated in FIGS. 7C and 7D, the container 16 is moved up by operating the sample stage while the block member 7 is kept stopped.

Then, as illustrated in FIG. 7E, when the container 16 is moved more upward, the block member 7 is also moved upward together with the sample liquid introducing member (suction nozzle 31). As a result, as illustrated in FIG. 7F, movement of the sample liquid introducing member (suction nozzle 31) is detected by the position detection sensor 41, and upward movement of the sample stage 5 (container 16) and the block member 7 is stopped.

Furthermore, the block member may have a cleaning function. Specifically, as illustrated in FIG. 8, a flow passage 17a is formed inside a block member 17, and while cleaning liquid is circulated in the flow passage 17a, the block member 17 is moved upward and downward along the outer surface of the suction nozzle 31. This enables cleaning for the outer surface of the suction nozzle 31.

Here, in the case of the block member 17 having the cleaning function, cleaning is performed by introducing the cleaning liquid into a penetration hole 17b penetrating the suction nozzle 31. Therefore, preferably, a diameter of a penetration hole 17b is formed slightly larger than an outer diameter of the suction nozzle 31. Furthermore, besides such outer surface cleaning by the above-described method, the block member 17 can perform cleaning also by allowing the cleaning liquid to flow from the flow cell 2 and sucking the cleaning liquid when the block member 17 performs backflow cleaning in which the cleaning liquid is discharged from the tip of the suction nozzle 31. Consequently, cleaning for the inner surface and the outer surface can be performed in a short time.

Since the block member is attached to the suction nozzle in the particle analyzer of the present embodiment, contact (impact) between the sample liquid introducing member (suction nozzle) and the container can be surely detected. Furthermore, since the block member is made to have the cleaning function, the outer surface of the suction nozzle can be cleaned. Therefore, there is no need to provide a separate cleaning facility, and the device can be simplified.

Configurations and effects other than those described above in the particle analyzer of the present embodiment are similar to the first embodiment described above.

Furthermore, the present technology may also have following configurations.

(1)

A particle analyzer, including:

a flow cell including: an introducing unit adapted to introduce sample liquid containing current analysis particles, and sheath liquid; and a detection unit in which a laminar flow formed of the sample liquid and the sheath liquid flows;

a sample liquid introducing member disposed immediately below the flow cell in a manner movable in a forward direction and a reverse direction relative to a sample liquid introducing direction, and formed by integrating a suction nozzle adapted to suck sample liquid with a sample liquid introducing nozzle disposed inside the introducing unit of the flow cell and adapted to discharge the sucked sample liquid into the flow cell; and a movement restriction mechanism adapted to restrict a moving amount of the sample liquid introducing member.

(2)

The particle analyzer recited in (1) above, wherein the movement restriction mechanism is a rib portion provided on an outer surface of the sample liquid introducing nozzle.

(3)

The particle analyzer recited in (1) or (2) above, wherein the movement restriction mechanism includes a position sensor adapted to detect positional change of the sample liquid introducing member, and a sample stage control unit adapted to control, on the basis of a detection result of the position sensor, movement of a sample stage on which a container storing the sample liquid is placed.

(4)

The particle analyzer recited in (3) above, wherein the sample stage control unit stops upward movement of the sample stage in the case where the position sensor detects upward movement of the sample liquid introducing member.

(5)

The particle analyzer recited in any one of (1) to (4), wherein the sample liquid introducing nozzle is fixed to the introducing unit of the flow cell via a spring material or an elastic material.

(6)

The particle analyzer recited in any one of (1) to (5) above, wherein a block member is attached to an outer surface of the suction nozzle.

(7)

The particle analyzer recited in (6) above, wherein the block member is moved upward and downward in accordance with upward movement and downward movement of the sample stage on which the container storing the sample liquid is placed.

(8)

The particle analyzer recited in (6) or (7) above, wherein a flow passage where cleaning liquid flows is formed inside the block member, and cleaning for the outer surface of the suction nozzle is performed by moving upward and downward along the outer surface of the suction nozzle.

Note that the above effects described in the present specification are only examples and not limited thereto, and further additional effects may be provided as well.

REFERENCE SIGNS LIST 1, 11 Particle analyzer
2 Flow cell
3 Sample liquid introducing member
4 Movement restriction mechanism
5 Sample stage
6, 16 Container
6a Lid
7, 17 Block member
10 Sample liquid
17a Flow passage
17b Penetration hole
21 Introducing unit
22 Detection unit
23 Spring material
24 Packing
25 Guide
31 Suction nozzle
32 Sample liquid introducing nozzle
32a Rib portion
41 Position detection sensor
51 Sample stage control unit
52 Motor
71 Cleaning liquid flow passage

The invention claimed is:

1. A particle analyzer, comprising:
a flow cell that comprises:
an introducing unit configured to introduce:
a sample liquid containing analysis particles, and
a sheath liquid; and
a detection unit in which the sample liquid and the sheath liquid flow in a laminar flow;
a sample liquid introducing member configured to move between a container and the flow cell in one of a forward direction or a reverse direction relative to a sample liquid introducing direction,
wherein the sample liquid introducing member is below the flow cell,
wherein the sample liquid introducing member includes:
a suction nozzle configured to suck the sample liquid from the container, and
a sample liquid introducing nozzle configured to discharge the sucked sample liquid into the flow cell, and
wherein the sample liquid introducing nozzle is inside the introducing unit of the flow cell; and
a movement restriction mechanism configured to restrict a moving amount of the sample liquid introducing member.

2. The particle analyzer according to claim 1, wherein the movement restriction mechanism is a rib portion on an outer surface of the sample liquid introducing nozzle.

3. The particle analyzer according to claim 1, wherein the movement restriction mechanism includes:
a position sensor configured to detect positional change of the sample liquid introducing member, and
a sample stage control unit configured to control, based on the positional change, movement of a sample stage,
wherein the sample liquid is stored in the container, and
wherein the container is on the sample stage.

4. The particle analyzer according to claim 3,
wherein the positional change is an upward movement of the sample liquid introducing member, and
wherein the sample stage control unit is further configured to stop an upward movement of the sample stage based on the upward movement of the sample liquid introducing member.

5. The particle analyzer according to claim 1, wherein the sample liquid introducing nozzle is attached to the introducing unit of the flow cell via one of a spring material or an elastic material.

6. The particle analyzer according to claim 1, further comprising a block member attached to an outer surface of the suction nozzle.

7. The particle analyzer according to claim 6,
wherein the block member is moved upward and downward based on upward movement and downward movement of a sample stage,
wherein the container is on the sample stage, and
wherein the sample liquid is stored in the container.

8. The particle analyzer according to claim 6,
wherein a flow passage where cleaning liquid flows is inside the block member, and
wherein the outer surface of the suction nozzle is cleaned by upward movement and downward movement of the block member along the outer surface of the suction nozzle.

9. A particle analyzer, comprising:
a flow cell including:
an introducing unit configured to introduce:
a sample liquid containing analysis particles, and
a sheath liquid; and
a detection unit in which the sample liquid and the sheath liquid flow in a laminar flow;
a sample liquid introducing member configured to move in one of a forward direction or a reverse direction relative to a sample liquid introducing direction,
wherein the sample liquid introducing member is below the flow cell,
wherein the sample liquid introducing member includes:

a suction nozzle configured to suck the sample liquid from a container, and
a sample liquid introducing nozzle configured to discharge the sucked sample liquid into the flow cell, and
wherein the sample liquid introducing nozzle is inside the introducing unit of the flow cell;
a movement restriction mechanism configured to restrict a moving amount of the sample liquid introducing member; and
a block member attached to an outer surface of the suction nozzle,
wherein the block member is moved upward and downward based on upward movement and downward movement of a sample stage,
wherein the container is on the sample stage, and
wherein the sample liquid is stored in the container.

10. A particle analyzer, comprising:
a flow cell including:
an introducing unit configured to introduce:
a sample liquid containing analysis particles, and
a sheath liquid; and
a detection unit in which the sample liquid and the sheath liquid flow in a laminar flow;
a sample liquid introducing member configured to move in one of a forward direction or a reverse direction relative to a sample liquid introducing direction,
wherein the sample liquid introducing member is below the flow cell,
wherein the sample liquid introducing member includes:
a suction nozzle configured to suck the sample liquid from a container, and
a sample liquid introducing nozzle configured to discharge the sucked sample liquid into the flow cell, and
wherein the sample liquid introducing nozzle is inside the introducing unit of the flow cell;
a movement restriction mechanism configured to restrict a moving amount of the sample liquid introducing member; and
a block member attached to an outer surface of the suction nozzle, wherein a flow passage where cleaning liquid flows is inside the block member, and wherein the outer surface of the suction nozzle is cleaned by upward and downward movement of the block member along the outer surface of the suction nozzle.

* * * * *